(12) United States Patent
Onda et al.

(10) Patent No.: US 6,417,408 B2
(45) Date of Patent: Jul. 9, 2002

(54) PRODUCTION PROCESS FOR (POLY)ALKYLENE GLYCOL MONOALKYL ETHER

(75) Inventors: Yoshiyuki Onda; Masaru Kirishiki, both of Suita; Hideaki Tsuneki, Shinagawa-ku; Yukio Kadono, Yokohama, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/790,053

(22) Filed: Feb. 21, 2001

Related U.S. Application Data

(60) Continuation of application No. 09/410,893, filed on Oct. 3, 1999, now abandoned, which is a division of application No. 08/980,577, filed on Dec. 1, 1997, now Pat. No. 5,994,595.

(30) Foreign Application Priority Data

Dec. 6, 1996 (JP) .............................. 8-342617
Dec. 6, 1996 (JP) .............................. 8-342618

(51) Int. Cl.$^7$ .............................. C07C 41/06
(52) U.S. Cl. .................. 568/678; 568/679; 568/697; 568/699
(58) Field of Search ................ 568/678, 679, 568/697, 699

(56) References Cited

U.S. PATENT DOCUMENTS

| | | |
|---|---|---|
| 3,965,207 A | 6/1976 | Weinstein |
| 4,139,566 A | 2/1979 | Kim et al. .................. 568/679 |
| 4,299,997 A | 11/1981 | Matsumoto et al. |
| 4,714,787 A | * 12/1987 | Bell et al. .................. 568/697 |
| 5,015,782 A | 5/1991 | Harandi et al. |
| 5,741,948 A | 4/1998 | Kirishiki et al. |
| 5,994,595 A | 11/1999 | Onda et al. |

FOREIGN PATENT DOCUMENTS

| | | |
|---|---|---|
| DE | 4222183 * | 1/1994 |
| EP | 0 309 177 A1 | 3/1989 |
| EP | 0 310 194 | 4/1989 |
| EP | 0 407 841 A2 | 1/1991 |
| EP | 0 419 077 A2 | 3/1991 |
| EP | 0 649 829 A1 | 4/1995 |
| EP | 0 718 270 A2 | 6/1996 |
| EP | 0 747 339 A1 | 12/1996 |
| JP | 46-10064 | 3/1971 |
| JP | 57-35687 | 7/1982 |
| JP | 61-51570 | 11/1986 |
| JP | 63250336 A | 10/1988 |
| JP | 2-295941 | 12/1990 |
| JP | 3-148233 | 6/1991 |
| JP | 9-52856 | 2/1997 |
| WO | WO 94/01389 | 1/1994 |

OTHER PUBLICATIONS

Meier et al., Atlas of Zeolite Structure Types, Jun., 1992, Contents page (p. 453) listing structure type data, vol. 12, No. 5, Butterworth–Heinemann, USA.

Szostak, R., Contents Page and Introduction, Handbook of Molecular Sieves, 1992, pp. vii, and xiii–xvi, Van Nostrand Reinhold, New York.

Ione et al., Synthesis of Crystalline Metal Silicates Having Zeolite Structure and Study of their Catalytic Properties, Journal of Molecular Catalysis, 1985, pp. 355–370, Elsevier Sequoia, The Netherlands.

Perez–Pariente et al., Factors affecting the synthesis efficiency of zeolite BETA from aluminosilicate gels containing alkali and tetraethylammonim ions, Zeolites, Jan., 1988, pp. 46–53, vol. 8, Butterworth Publishers.

\* cited by examiner

*Primary Examiner*—Rosalynd Keys

(57) ABSTRACT

The present invention provides a process for producing a (poly)alkylene glycol monoalkyl ether with high selectivity and high yield. In this process, the (poly)alkylene glycol monoalkyl ether is produced by reacting an olefin and a (poly)alkylene glycol in the presence of a catalyst, wherein: 1) a crystalline metallosilicate is used as the catalyst, and at least a portion of the used catalyst is regenerated, and the regenerated catalyst is recycled as the catalyst for the reaction; or 2) the reaction between the olefin and the (poly)alkylene glycol is carried out in the presence of either or both of a (poly)alkylene glycol dialkyl ether and an alcohol.

2 Claims, 2 Drawing Sheets

PRODUCTION PROCESS FOR (POLY)ALKYLENE GLYCOL MONOALKYL ETHER

This application is a continuation of 09/410,893, filed Oct. 3, 1999, now abandoned which is a divisional of 08/980,577, filed Dec. 1, 1997, now U.S. Pat. No. 5,994,595.

BACKGROUND OF THE INVENTION

A. Technical Field

The present invention relates to a production process for a (poly)alkylene glycol monoalkyl ether.

B. Background Art

As to processes for producing a (poly)alkylene glycol monoalkyl ether by reacting an olefin and a (poly)alkylene glycol, for example, the following processes are disclosed: a process in which strong acid cation-exchange resins are used as the catalyst (e.g. Japanese Allowable Patent Publication (Kokoku) No. 57-35687 and Japanese Patent Application Publication (Kokai) No. 2-295941); a process in which heteropolyacids are used as the catalyst (Japanese Patent Application Publication (Kokai) No. 3-148233); and a process in which benzenesulfonic acid or toluenesulfonic acid is used as the catalyst (Japanese Allowable Patent Publication (Kokoku) No. 61-51570).

However, where the strong acid cation-exchange resins, the heteropolyacids, the benzenesulfonic acid, or the toluenesulfonic acid is used as the catalyst, there are problems in that because the (poly)alkylene glycol which is a raw material is a diatomic alcohol, the reaction tends to involve a dehydration polycondensation reaction or dehydration cyclization reaction of the (poly)alkylene glycol itself as a side reaction to form water, and this formed water tends to react upon the olefin to form an alcohol as a by-product, so the resultant selectivity to the (poly)alkylene glycol monoalkyl ether is extremely low. For instance, examples of some preferred embodiments as set forth in the Japanese Patent Application Publication (Kokai) No. 2-295941 disclose that when ethylene glycol and dodecene are reacted using Nafion H (fluorine-containing strong acid ion-exchange resin), made by E. I. Du Pont DE NEMOURS & Co., Ltd., as the catalyst to produce ethylene glycol monododecyl ether, dodecanol forms as a by-product in a proportion of 7 to 10 mol % of the ethylene glycol monododecyl ether.

SUMMARY OF THE INVENTION

A. Objects of the Invention

An object of the present invention is to provide a process for producing a (poly)alkylene glycol monoalkyl ether with high selectivity.

B. Disclosure of the Invention

The present inventors diligently studied to attain the above-mentioned object, and as a result, found that if a crystalline metallosilicate is used as the catalyst, or if the reaction between the olefin and the (poly)alkylene glycol is carried out in the presence of an alcohol, the resultant selectivity to the (poly)alkylene glycol monoalkyl ether is high, in other words, that if a catalyst with high catalytic activity such as the crystalline metallosilicate is used, not only can the selectivity be raised, but also does the reaction rate become fast to lead to the increase in the conversion, or if the alcohol which will be a by-product is added into the reaction system, the side reaction can be inhibited due to the principle of equilibrium reaction.

By the way, the inventors further got the below-mentioned two findings:

First, it was found that the addition reaction of the olefin upon the (poly)alkylene glycol includes not only a reaction of the formation of the (poly)alkylene glycol monoalkyl ether from the (poly)alkylene glycol, but also a reaction of formation of a (poly)alkylene glycol dialkyl ether. The activity of prior art catalysts is low, and no prior art disclosed the formation of the (poly)alkylene glycol dialkyl ether. However, it became clear that where a high active catalyst such as the crystalline metallosilicate is used, the (poly)alkylene glycol dialkyl ether also forms, so the resultant selectivity of the (poly)alkylene glycol monoalkyl ether is low. Therefore, it was found that when the olefin and the (poly)alkylene glycol are reacted to produce the (poly)alkylene glycol monoalkyl ether, it is effective to add the (poly)alkylene glycol dialkyl ether to inhibit the formation thereof as well.

Secondly, the crystalline metallosilicate has a problem in that where it is used for a reaction, its catalytic activity decreases with time. Thus, to solve this problem, the present inventors found that if at least a portion of the used catalyst is regenerated and then recycled as the catalyst for the reaction, the stationary activity of the catalyst can be obtained. As a result, the inventors completed the present invention.

That is to say, a process for producing a (poly)alkylene glycol monoalkyl ether, according to a first embodiment of the present invention, comprises the step of reacting a (poly)alkylene glycol and an olefin in the presence of a catalyst, thus obtaining the (poly)alkylene glycol monoalkyl ether, with the process being characterized in that a crystalline metallosilicate is used as the catalyst, and further characterized by further comprising the steps of: regenerating at least a portion of the used catalyst; and recycling the regenerated portion of the used catalyst as the catalyst for the reaction between the (poly)alkylene glycol and the olefin (herein, this production process is referred to as "first production process").

In the first production process of the present invention, it is preferable that the regeneration of the catalyst is carried out by thermal treatment of the catalyst at 450° C. or higher under an oxygen-containing gas atmosphere. In addition, it is preferable that the crystalline metallosilicate is a BEA type metallosilicate. In addition, it is preferable that at least a portion of a slurry containing the catalyst and an unreacted residue of the (poly)alkylene glycol is extracted, and that the catalyst is then recovered from the slurry to regenerate the catalyst. In addition, it is preferable that when the catalyst is recovered from the slurry, the (poly)alkylene glycol is also recovered from the slurry by distillation under temperature conditions of 180° C. or lower, or that when the catalyst is recovered from the slurry, the (poly)alkylene glycol is also recovered from the slurry by distillation within 30 minutes. In addition, it is preferable that a long chain olefin is used as the olefin, when a (poly)alkylene glycol mono-higher-alkyl ether is obtained as the (poly)alkylene glycol monoalkyl ether. In addition, it is preferable that the regeneration of at least a portion of the used catalyst is carried out after the catalyst is used for 0.02 to 100 hours for the reaction.

A process for producing a (poly)alkylene glycol monoalkyl ether, according to a second embodiment of the present invention, comprises the step of reacting an olefin and a (poly)alkylene glycol in the presence of a catalyst, thus obtaining the (poly)alkylene glycol monoalkyl ether, with the process being characterized in that the reaction between the olefin and the (poly)alkylene glycol is carried out in the presence of either or both of a (poly)alkylene glycol dialkyl ether and an alcohol (herein, this production process is referred to as "second production process").

In addition, the second production process of the present invention may be further characterized by further comprising the steps of:

recovering either or both of the (poly)alkylene glycol dialkyl ether and the alcohol, both of which form as by-products in the reaction between the olefin and the (poly)alkylene glycol; and recycling the recovered either or both of the (poly)alkylene glycol dialkyl ether and the alcohol to a system of the reaction between the olefin and the (poly)alkylene glycol.

In addition, the second production process of the present invention may be further characterized by further comprising the steps of:

recovering the resultant olefin phase and the resultant (poly)alkylene glycol phase after the reaction; and separating the (poly)alkylene glycol monoalkyl ether from the olefin phase.

In addition, the second production process of the present invention may be further characterized by further comprising the step of recovering either or both of the (poly)alkylene glycol dialkyl ether and the alcohol, both of which form as by-products, from the olefin phase after the reaction.

In addition, the second production process of the present invention may be further characterized by further comprising the steps of:

recovering an unreacted residue of the olefin after the reaction; and recycling the unreacted residue of the olefin to the reaction with the (poly)alkylene glycol.

In addition, the second production process of the present invention may be further characterized by further comprising the step of recycling a (poly)alkylene glycol phase, resultant from the reaction and including the catalyst, to the reaction with the olefin.

In addition, the second production process of the present invention may be further characterized in that a crystalline metallosilicate is used as the catalyst.

In addition, the second production process of the present invention may be further characterized in that: the (poly)alkylene glycol monoalkyl ether is a (poly)alkylene glycol mono-higher-alkyl ether; the olefin is a long chain olefin; the (poly)alkylene glycol dialkyl ether is a (poly)alkylene glycol di-higher-alkyl ether; and the alcohol is a higher alcohol.

These and other objects and the advantages of the present invention will be more fully apparent from the following detailed disclosure.

DETAILED DESCRIPTION OF THE INVENTION

Figure 1:
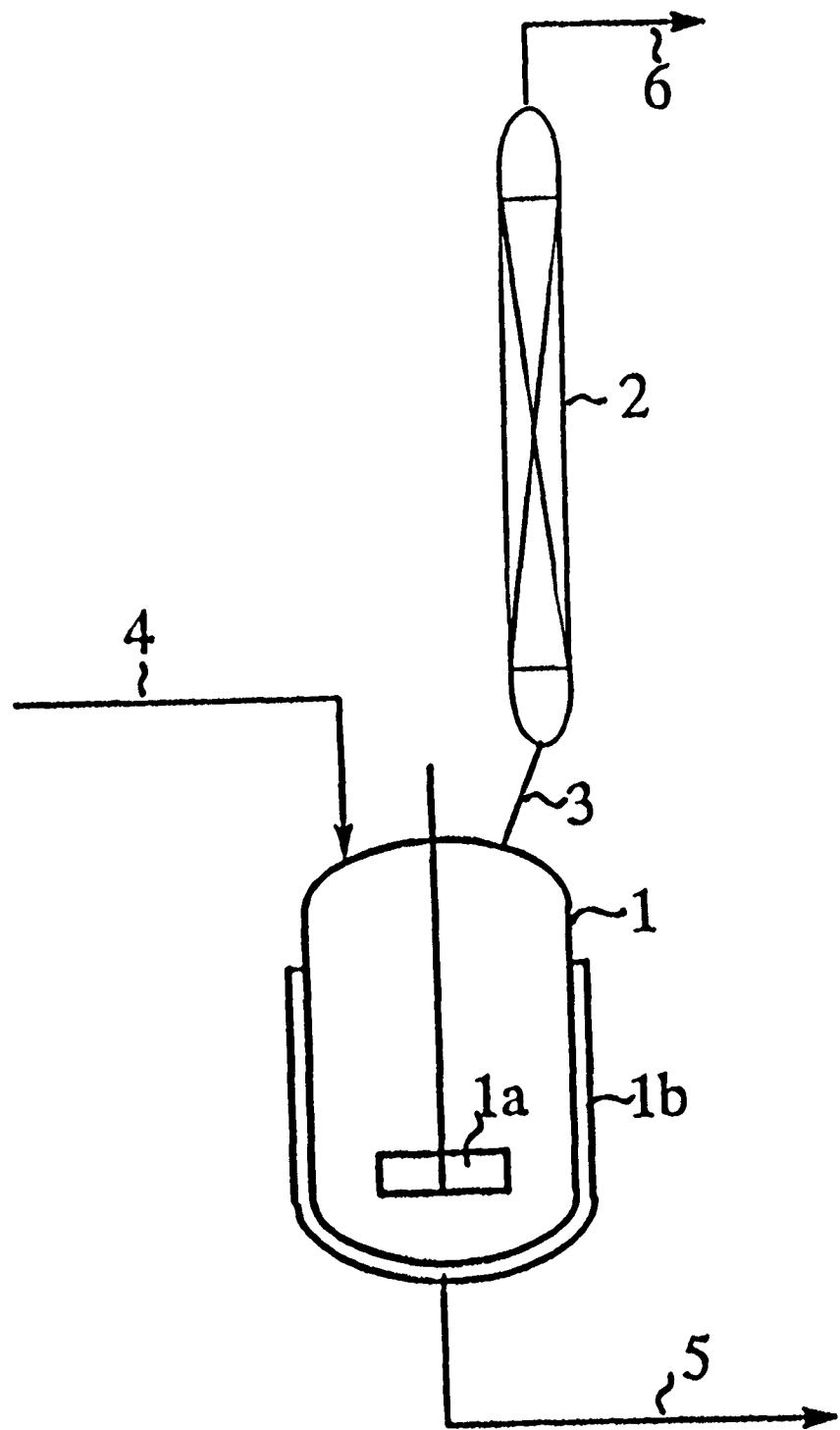
FIG. 1 shows an example of flow charts of reaction apparatuses with a batch type reactor.

Preferable examples of the olefin, as used in the present invention, include hydrocarbons of 2 to 40, more preferably, 8 to 30, still more preferably, 10 to 20, in number of carbon atoms with an ethylenically unsaturated bond. Among the olefins, particularly, long chain olefins are preferable. When the long chain olefin is used as the olefin, the resultant (poly)alkylene glycol monoalkyl ether is a (poly)alkylene glycol mono-higher-alkyl ether, the (poly)alkylene glycol dialkyl ether is a (poly)alkylene glycol di-higher-alkyl ether, and the alcohol is a higher alcohol. Preferable examples of the long chain olefin include hydrocarbons of 8 to 30, more preferably, 10 to 20, in number of carbon atoms with an ethylenically unsaturated bond.

Even if the olefins are branched ones, linear chain ones, acyclic ones, cyclic ones, or mixtures thereof, they can be used with no especial limitation. Considering the use for surfactants, however, it is preferable that the olefin comprises an acyclic olefin, more preferably, a linear chain olefin, as the main component. Specific examples thereof include octene, decene, dodecene, tetradecene, hexadecene, octadecene, icosene, docosene. These olefins, of which the position of the unsaturated bond is α-position, inner position, or both them, can be used with no especial limitation. Of course, two or more olefins which are different from each other with regard to the position of the unsaturated bond can be used in combination. The process of the reaction in the present invention involves a reaction in which the olefin isomerizes with regard to the position of the unsaturated bond. An inner olefin is generally thermodynamically more stable than an α-olefin, and therefore, when the α-olefin is used as a raw material, it gradually isomerizes to the inner olefin during the reaction. The speed of the isomerization depends on the reaction temperature or the type or amount of the catalyst.

Examples of the (poly)alkylene glycol, as used in the present invention, include monoethylene glycol, diethylene glycol, triethylene glycol, polyethylene glycol, monopropylene glycol, dipropylene glycol, tripropylene glycol, polypropylene glycol, 1,3-propanediol, 1,2-butanediol, 2,3-b utanediol, 1,4-butanediol, 1,6-hexanediol, 1,4-cyclohexanemethanediol. These may be used either alone or in combinations of two or more thereof.

Acid catalysts are suitable for the catalyst as used in the present invention. Examples of thereof include: homogeneous catalysts such as sulfuric acid, benzenesulfonic acid, dodecylbenzenesulfonic acid, and heteropolyacids (e.g. phosphotungstic acid, phosphomolybdic acid, silicotungstic acid, silicomolybdic acid); acid ion-exchange resins; complex metal oxides such as silica-alumina and titania-silica; and zeolite. These catalysts may be used either alone or in combinations of two or more thereof.

Among them, particularly, crystalline metallosilicates are preferable. The crystalline metallosilicate is a regular porous substance having a certain crystal structure, in other words, a solid substance having many regular interstices or pores in the structure and a large specific surface area.

Examples of the crystalline metallosilicate, as used in the present invention, include crystalline aluminosilicate (which may be commonly called zeolite) and compounds in which another metal element is introduced into a crystal lattice in place of the Al atom of the crystalline aluminosilicate. Specific examples of the another metal element include B, Ga, In, Ge, Sn, P, As, Sb, Sc, Y, La, Ti, Zr, V, Cr, Mn, Fe, Co, Ni, Cu, Zn. These may be used either alone or in combinations of two or more thereof. Considering the catalytic activity and the ease of the synthesis or availability, crystalline aluminosilicate, crystalline ferrosilicate, crystalline borosilicate, and crystalline gallosilicate are preferable, and particularly, crystalline aluminosilicate is favorable.

Specific examples of the crystalline metallosilicate, as used in the present invention, include those which have structures such as MFI (e.g. ZSM-5), MEL (e.g. ZSM-11), BEA (e.g. β-type zeolite), FAU (e.g. Y-type zeolite), MOR (e.g. Mordenite), MTW (e.g. ZSM-12), and LTL (e.g. Linde L), as described using IUPAC codes in accordance with nomenclature by the Structure Commission of the International Zeolite Association, and further, those which have structures as disclosed in "ZEOLITES, Vol. 12, No. 5, 1992" or "HANDBOOK OF MOLECULAR SIEVES, written by R. Szostak, published by VAN NOSTRAND REINHOLD." These may be used either alone or in combinations of two or more thereof. Among them, such as has a BEA structure is particularly preferable, considering its excellent catalytic activity.

A preferable example of the crystalline metallosilicate, as used in the present invention, is such in which the atomic ratio of the silicon atom to the metal atom, constituting the crystalline metallosilicate, is in the range of 5 to 1,500, more preferably, 10 to 500. Where the atomic ratio of the silicon atom to the metal atom is too small or too large, the catalytic activity is unfavorably low.

The crystalline metallosilicate has an ion-exchangeable cation outside the crystal lattice. Specific examples of such a cation include $H^+$, $Li^+$, $Na^+$, $Rb^+$, $Cs^+$, $Mg^{2+}$, $Ca^{2+}$, $Sr^{2+}$, $Ba^{2+}$, $Sc^{3+}$, $Y^{3+}$, $La^{3+}$, $R_4N^+$, $R_4P^+$ (R is H or alkyl). Particularly, a crystalline metallosilicate in which the cation is partially or entirely replaced with a hydrogen ion is favorable as the catalyst in the present invention.

The crystalline metallosilicate, as used in the present invention, can be synthesized by conventionally used synthesis methods such as hydrothermal synthesis methods, specifically, by methods as disclosed in Japanese Allowable Patent Publication (Kokoku) No. 46-10064; U.S. Pat. No. 3,965,207; "The Journal of Molecular Catalysis," Vol. 31, pp. 355–370 (published in 1985); and Zeolites, Vol. 8, p. 46 (published in 1988). The crystalline metallosilicate, for example, can be synthesized in the following way: a composition comprising a silica source, a metal source, and a quaternary ammonium salt such as a tetraethylammonium salt or tetrapropylammonium salt is heated at a temperature of about 100 to about 175° C. until a crystal forms, and the resultant solid product is then filtered off, washed with water, and dried, and then calined at 350–600° C. Metallosilicates of different crystal systems can be obtained by fitly adjusting raw materials or synthesis conditions.

Examples of the aforementioned silica source include water glass, silica sol, silica gel, and alkoxysilanes. Examples of the aforementioned metal source include various inorganic or organic metal compounds. Preferable examples of the metal compound include: metal salts such as metal sulfates (e.g. $Al_2(SO_4)_3$), metal nitrates (e.g. $Fe(NO_3)_3$), and alkaline metal salts of metal oxides (e.g. $NaAlO_2$); metal halides such as metal chlorides (e.g. $TiCl_4$) and metal bromides (e.g. $MgBr_2$); and metal alkoxides (e.g. $Ti(OC_2H_5)_4$). The resultant crystalline metallosilicate can be converted into an objective cation matter by ion-exchange, if necessary. For example, an $H^+$ type cation matter can be prepared in the following way: the crystalline metallosilicate is mixed by stirring in an aqueous solution of HCl, $NH_4Cl$, or $NH_3$ to exchange the cation species with an $H^+$ type or $NH_4+$ type, and the resultant solid product is then filtered off, washed with water, and dried, and then calcined at 350–600° C. Cation matters other than the $H^+$ type can be prepared by carrying out the same procedure as the above-mentioned one using an aqueous solution containing an objective cation.

As to the crystalline metallosilicate, either crystalline metallosilicates of sole crystal systems or crystalline metallosilicates of combinations of various crystal systems may be used.

The crystalline metallosilicate may be jointly used with conventional catalysts such as sulfuric acid, heteropolyacids, benzenesulfonic acid, and ion-exchange resins.

In the present invention, the catalyst may be used in any form, and, for example, powdered ones, granular ones, or molded matters of specific shapes can be used. In addition, where the molded matter is used, examples of carriers or binders of the molded matter indude alumina, silica, and titania. In addition, where a homogeneous catalyst is used as the catalyst, it can be used in a dissolved state in a raw reaction material.

The (poly)alkylene glycol dialkyl ether, as used in the second production process of the present invention, is resultant from a further addition reaction of the olefin upon the (poly)alkylene glycol monoalkyl ether, which is the objective product in the second production process of the present invention, or resultant from a condensation reaction between (poly)alkylene glycol monoalkyl ethers, and is a substance as obtained as a by-product when the olefin and the (poly)alkylene glycol are reacted in the presence of a catalyst to produce the (poly)alkylene glycol monoalkyl ether. The alcohol, as used in the second production process of the present invention, is a substance as obtained as a by-product by an addition reaction of a water content in the reaction system upon the olefin when the olefin and the (poly)alkylene glycol are reacted in the presence of a catalyst to produce the (poly)alkylene glycol monoalkyl ether.

In the second production process of the present invention, if either or both of the (poly)alkylene glycol dialkyl ether and the alcohol, both of which form as by-products, are supplied to a system of the reaction between the olefin and the (poly)alkylene glycol, the (poly)alkylene glycol monoalkyl ether can be obtained efficiently.

The reason why the (poly)alkylene glycol monoalkyl ether can be obtained efficiently by supplying the (poly)alkylene glycol dialkyl ether to the reaction system can be explained as follows: It seems that between the olefin<=>the (poly)alkylene glycol monoalkyl ether<=>the (poly)alkylene glycol dialkyl ether, there are the following equilibrium relations:

$$OL+PAG<=>M \qquad (1)$$

$$OL+M<=>D \qquad (2)$$

$$M+M<=>D+PAG \qquad (3)$$

wherein: OL is the olefin, PAG is the (poly)alkylene glycol, M is the (poly)alkylene glycol monoalkyl ether, and D is the (poly)alkylene glycol dialkyl ether; and that the addition reaction, the condensation reaction, and reverse reactions of them run simultaneously. Thus, if the (poly)alkylene glycol dialkyl ether is supplied to the reaction system, reverse reactions of (2) and (3) above run, thus obtaining the (poly)alkylene glycol monoalkyl ether. In addition, if the (poly)alkylene glycol dialkyl ether, which forms as a by-product in the reaction between the olefin and the (poly)alkylene glycol, is recovered and supplied (recycled) to the next reaction to carry out the reaction, substantially only the (poly)alkylene glycol monoalkyl ether can be selectively obtained from the olefin and the (poly)alkylene glycol.

The reason why the (poly)alkylene glycol monoalkyl ether can be obtained efficiently by supplying the alcohol to the reaction system can be explained as follows: It seems that between the olefin<=>the alcohol, there is the following equilibrium relation:

$$OL+H_2O<=>AL \qquad (4)$$

wherein: OL is the olefin and AL is the alcohol; and that the hydration reaction and the reverse reaction thereof run simultaneously. Thus, if the alcohol is supplied to the reaction system, the reverse reaction of (4) above runs, thus obtaining the olefin that is a raw material. In addition, if the alcohol, which forms as a by-product in the reaction between the olefin and the (poly)alkylene glycol, is recovered and supplied (recycled) to the next reaction to carry out the reaction, substantially only the (poly)alkylene glycol monoalkyl ether can be selectively obtained from the olefin and the (poly)alkylene glycol.

The reaction between the olefin and the (poly)alkylene glycol in the present invention can be carried out either in the presence of or in the absence of a solvent. Examples of the solvent, as can be used, include nitromethane, nitroethane, nitrobenzene, dioxane, ethylene glycol dimethyl ether, sulfolane, benzene, toluene, xylene, hexane, cyclohexane, decane, paraffin.

The reaction between the olefin and the (poly)alkylene glycol in the present invention can be carried out in conventionally used manners such as batch type reactions and flow type reactions, and is not especially limited. The molar ratio between the olefin and the (poly)alkylene glycol, which are raw reaction materials, is not especially limited, but is preferably in the range of 0.05 to 20, more preferably, 0.1 to 10, as the molar ratio of the (poly)alkylene glycol to the olefin. The reaction temperature is preferably in the range of 50 to 250° C., more preferably, 100 to 200° C., and the reaction pressure may be any of a reduced one, a normal one, and an increased one, but it is preferably in the range from a normal pressure to 20 kg/cm$^2$.

The respective amounts of the (poly)alkylene glycol dialkyl ether and the alcohol, either or both of which are supplied to the system of the reaction between the olefin and the (poly)alkylene glycol in the second production process, is not especially limited. The (poly)alkylene glycol dialkyl ether or the alcohol, both of which form as by-products, may be recovered and accumulated, and then supplied to the reaction system at once, or the (poly)alkylene glycol dialkyl ether or the alcohol, resultant from the previous reaction as by-products, may always be supplied to the next reaction. When the flow type reaction is carried out to continuously produce the (poly)alkylene glycol monoalkyl ether, it is preferable that the (poly)alkylene glycol dialkyl ether or the alcohol, both of which form as by-products, is continuously recovered and always supplied by recycling to the reaction system. The amount of the formation of the (poly)alkylene glycol dialkyl ether or the alcohol, both of which form as by-products in the reaction between the olefin and the (poly)alkylene glycol, depends on factors such as the types or molar ratio of the olefin and the (poly)alkylene glycol, the type of the catalyst as used, the reaction temperature, or the reaction period of time, but the amount is usually in the range of 0.0001 to 30 mol % of the olefin which is a raw material. In addition, both the (poly)alkylene glycol dialkyl ether and the alcohol substantially might not form as by-products, depending on factors such as the type of the catalyst or the types of the raw materials as used or reaction conditions. Furthermore, either the (poly)alkylene glycol dialkyl ether or the alcohol, both of which form as by-products, might be recovered as a product. In these cases, it is enough for the present invention to supply only either the (poly)alkylene glycol dialkyl ether or the alcohol to the system of the reaction between the olefin and the (poly) alkylene glycol.

Where a batch type reactor is used, the catalyst and the raw materials are charged into the reactor, and the agitation is carried out at a predetermined temperature under a predetermined pressure, thus obtaining a mixture containing the objective (poly)alkylene glycol monoalkyl ether. The amount of the catalyst, as used, is not especially limited, but is preferably in the range of 0.1 to 100 wt %, more preferably, 0.5 to 50 wt %, of the olefin which is a raw material. The reaction period of time depends on factors such as the reaction temperature, the amount of the catalyst, or the ratio of the composition of the raw materials, but is preferably in the range of 0.1 to 100 hours, more preferably, 0.5 to 30 hours.

Where a flow type reactor is used, the reaction can be carried out in any of a fluidized bed manner, an entrained bed manner, a fixed bed manner, and a stirred vessel manner. Reaction conditions depend on factors such as the composition of the raw materials, the concentration of the catalyst, or the reaction temperature, but the liquid hourly space velocity (LHSV), namely, the value as obtained by dividing the volume flow rate of the flowing raw materials by the volume of the reactor, is preferably in the range of 0.01 to 50 hr$^{-1}$, more preferably, 0.1 to 20 hr$^{-1}$.

In the first production process of the present invention, at least a portion of the used catalyst is regenerated (preferably after the catalyst is used for 0.02 to 100 hours for the reaction) and then recycled as the catalyst for the reaction between the (poly)alkylene glycol and the olefin. Where an unregenerated portion of the catalyst is present, the regenerated portion of the catalyst can be used in combination with the unregenerated portion of the catalyst. The catalyst loses its activity with time, but if at least a portion of the used catalyst is regenerated and then recycled in the above-mentioned way, the stationary activity can be obtained. The form of the recycling is not especially limited even if it is either in a continuous manner or in a batch manner. The preferable amount of the regeneration of the catalyst depends on the amount of the catalyst as used in the reaction or on reaction conditions, but is in the range of 0.5 wt % or more, further preferably, 1 wt % or more, of the amount of the used catalyst in the reaction. Where the amount of the regeneration is less than 0.5 wt %, the activity of the catalyst cannot be maintained, so the reaction rate and the productivity are unfavorably deteriorated. The upper limit of the amount of the regeneration is not especially restricted, and the entirety of the catalyst may be regenerated, but because the regeneration of the catalyst takes costs, the amount of the regeneration is preferably suppressed to 50 wt % or less, more preferably, 30 wt % or less.

In the first production process of the present invention, the (poly)alkylene glycol and the olefin, which are raw materials, merely dissolve into each other with a slight solubility, and in many cases, therefore, the crystalline metallosilicate which is the catalyst is mainly contained in the (poly)alkylene glycol phase, and the (poly)alkylene glycol monoalkyl ether which is a product is mainly contained in the olefin phase. Thus, in the first production process of the present invention, it is preferable that: after the reaction has ended, the (poly)alkylene glycol phase and the olefin phase are separated from each other, and at least a portion of the catalyst is extracted from the (poly)alkylene glycol phase containing the catalyst (i.e. a slurry containing the catalyst and an unreacted residue of the (poly)alkylene glycol), and then regenerated, and then recycled to the next reaction between the (poly)alkylene glycol and the olefin. The rest of the (poly)alkylene glycol phase, from which at least a portion of the catalyst is extracted, can be replenished with the (poly)alkylene glycol, as consumed in the reaction or lost when extracting the catalyst, and then recycled to the next reaction with the olefin. In addition, an unreacted residue of the olefin and the objective (poly)alkylene glycol monoalkyl ether can be recovered from the olefin phase by separation methods such as distillation, and the unreacted residue of the olefin can be then recycled to the next reaction.

The method for recovering the catalyst for the regeneration in the first production process is not especially limited, but the catalyst can be recovered from the reaction liquid by methods such as filtration, centrifugal separation, and drying. As is aforementioned, the form of the use of the catalyst as used in the first production process of the present invention is not especially limited, but it is preferable for raising the reaction rate that the catalyst is used in a state of a slurry in which the catalyst is suspended as fine particles in the (poly)alkylene glycol phase. Where such a form of the use is wanted, the separation of the catalyst from the (poly) alkylene glycol phase by the filtration or by the centrifugal separation involves the difficulty. In such a case, a preferable method is a method in which the (poly)alkylene glycol is distilled off from the slurry containing the (poly)alkylene glycol and the catalyst, thereby separating and recovering the catalyst. In such a method, the distilled (poly)alkylene glycol can be recovered and then recycled to the reaction system. When the (poly)alkylene glycol is distilled off from the slurry, because the catalyst (crystalline metallosilicate) is an acid catalyst, the catalyst runs unfavorable reactions such as a condensation reaction of the (poly)alkylene glycol where treated under high temperature conditions, and as a result, the recovery ratio of the (poly)alkylene glycol decreases.

It is a condition for distilling off and recovering the (poly)alkylene glycol in a high recovery ratio by inhibiting the unfavorable reactions such as the condensation reaction that temperature conditions fall within the range of 180° C. or lower, preferably, 150° C. or lower. If a pressure under which the (poly)alkylene glycol boils or a lower pressure is set under the above-mentioned temperature conditions, the (poly)alkylene glycol can be distilled off and recovered from the slurry efficiently. Where the catalyst and the (poly)alkylene glycol are recovered using a batch type evaporator or dryer, the time of the contact between the catalyst and the (poly)alkylene glycol (residence time) is so long that unfavorable reactions such as the above-mentioned condensation reaction tend to occur. It is especially preferable for inhibiting such reactions that the above-mentioned temperature conditions are applied. Apparatuses for recovering the catalyst or (poly)alkylene glycol are not limited to the above-mentioned batch type evaporator or dryer, but examples thereof include vacuum dryers such as centrifugal thin film types, rotary drum types, conical ribbon types, belt types, and fluidized bed types.

It is another condition for distilling off and recovering the (poly)alkylene glycol in a high recovery ratio by inhibiting the unfavorable reactions such as the condensation reaction that the time, as needed for distilling off and recovering the (poly)alkylene glycol, is shortened within 30 minutes, preferably, within 15 minutes, more preferably, within 5 minutes, and still more preferably, that the (poly)alkylene glycol is separated from the catalyst and recovered by distilling off the (poly)alkylene glycol almost in a moment. On such a occasion, it can be conditioned that the temperature is 400° C. or lower, preferably, 300° C. or lower, and that the pressure is normal pressure or vacuum. Apparatuses for recovering the catalyst or (poly)alkylene glycol are not especially limited, but examples thereof include continuous type dryers such as centrifugal thin film evaporators, instantaneous vacuum dryers, flash dryers, spray dryers, and fluidized bed dryers.

In the first production process of the present invention, methods for regenerating the catalyst are not especially limited, but a preferable one is a method in which the catalyst is subjected to thermal treatment under an oxygen-containing gas atmosphere. The thermal treatment temperature is preferably 450° C. or higher, more preferably, 500° C. or higher, still more preferably, 550° C. or higher. Where the thermal treatment temperature is lower than 450° C., a coke content remains in the catalyst, so the catalytic activity is not restored. In addition, the upper limit of the thermal treatment temperature is a temperature at which the structure of the crystalline metallosilicate is not destroyed, for example, generally 900° C. or lower, preferably 800° C. or lower, more preferably 700° C. or lower, still more preferably 650° C. or lower. Apparatuses as used for the thermal treatment not especially limited, but examples thereof include calcination furnaces such as rotary kilns, box furnaces, fluidized bed furnaces, roller-hearth kilns, mesh belt furnaces, and tray pusher furnaces.

The used catalyst can be directly subjected to the thermal treatment under an oxygen-containing gas atmosphere. Where the catalyst contains a large amount of organic substances such as an unrecovered portion of the (poly)alkylene glycol, however, the thermal treatment under an oxygen-containing gas atmosphere might cause ignition leading to high temperature, or the catalyst might be deteriorated by the influence of steam as contained in a combustion gas generating due to the combustion. In such a case, it is preferable that: the recovered catalyst is once subjected to thermal treatment in an inert gas to evaporate or decompose the organic substances, thus removing them from the catalyst, and the coke residue is then subjected to the above-mentioned thermal treatment under an oxygen-containing gas atmosphere, thus regenerating the catalyst.

In the second production process, the reaction liquid usually separates into two phases because the (poly)alkylene glycol and the olefin, which are raw materials, merely dissolve into each other with a slight solubility. In addition, the catalyst (e.g. crystalline metallosilicates) is mainly contained in the (poly)alkylene glycol phase, and the (poly)alkylene glycol monoalkyl ether, which is a product, and either or both of the (poly)alkylene glycol dialkyl ether and the alcohol, both of which are by-products, are mainly contained in the olefin phase. Therefore, after the reaction has ended, the (poly)alkylene glycol phase and the olefin phase are separated from each other, and the objective (poly)alkylene glycol monoalkyl ether can be obtained from the olefin phase by methods such as distillation and extraction. In addition, an unreacted residue of the olefin can be recovered, and then recycled to the next reaction with the (poly)alkylene glycol. Furthermore, either or both of the (poly)alkylene glycol dialkyl ether and the alcohol, both of which are by-products, can be recovered and then, as aforementioned, supplied and recycled to the system of the reaction between the olefin and the (poly)alkylene glycol. The olefin generally has the lowest boiling point of the unreacted olefin, the alcohol, the (poly)alkylene glycol monoalkyl ether, and the (poly)alkylene glycol dialkyl ether, and their boiling points become higher in order of the alcohol, the (poly)alkylene glycol monoalkyl ether, and the (poly)alkylene glycol dialkyl ether. Accordingly, the unreacted olefin and the alcohol can be first recovered as fractions by distillation, and the (poly)alkylene glycol monoalkyl ether can be then recovered as the product, and the (poly)alkylene glycol dialkyl ether can be either recovered as the distillation bottom or purified by further distillation, and the unreacted olefin and either or both of the (poly)alkylene glycol dialkyl ether and the alcohol, both of which are by-products, can be recycled to the system of the reaction between the olefin and the (poly)alkylene glycol. In addition, a portion of the distillation bottom may be discarded to purge impurities such as heavy, middle, or light contents, and the rest may be supplied and recycled to the system of the reaction between the olefin and the (poly) alkylene glycol. In detail, the impurities in the olefin phase include: light contents such as skeletal isomers of the olefin, condensation decomposition products of the (poly)alkylene glycol (e.g. dioxane, methyldioxolane); middle contents such as dimers of the olefin; or heavy contents such as polymers of the olefin; and these impurities can be separated and removed by fitly purifying the recovered olefin or (poly)alkylene glycol dialkyl ether by methods such as distillation.

Also in the second production process, the catalyst can be separated from the (poly)alkylene glycol phase containing the catalyst by methods such as centrifugal separation, filtration, and drying, and then recycled to the next reaction. In addition, the (poly)alkylene glycol can be recovered from the (poly)alkylene glycol phase by methods such as distillation, and then recycled to the next reaction with the olefin. It is preferable for simplifying the process to replenish the (poly)alkylene glycol phase, containing the catalyst, with the (poly)alkylene glycol, as consumed by the reaction, and to then recycle the (poly)alkylene glycol phase to the next reaction with the olefin. Where the catalyst is gradually deactivated due to the reaction, at least a portion of the catalyst can be extracted, and then regenerated or newly replenished, and then supplied to the next reaction. In addition, where impurities such as heavy contents or water accumulate in the (poly)alkylene glycol phase, a portion of the (poly)alkylene glycol phase may be extracted to purge the impurities, and the rest may be recycled to the next reaction. The heavy contents, such as high molecular polyalkylene glycol as formed by condensation of the (poly) alkylene glycol, can be removed by 1) a method in which a portion of the (poly)alkylene glycol phase is purged or 2) a method in which when the catalyst is recovered from the (poly)alkylene glycol phase and then regenerated, the heavy contents are allowed to remain in the catalyst and then removed by incineration during the regeneration of the catalyst, and/or in which when the catalyst is recovered from the (poly)alkylene glycol phase and then regenerated, the heavy contents are removed from the recovered (poly) alkylene glycol by purification by means such as distillation or adsorption. In addition, water, as formed by dehydration condensation of the (poly)alkylene glycol, can be removed by 1) a method in which a portion of the (poly)alkylene glycol phase is purged or 2) a method in which when the catalyst is recovered from the (poly)alkylene glycol phase and then regenerated, water is removed from the recovered (poly)alkylene glycol by purification by means such as distillation or adsorption.

Next, an explanation is made about embodiments of the present invention in accordance with the drawings. First, referring to FIG. 1, an explanation is made about an embodiment of the production process for the (poly)alkylene glycol monoalkyl ether using a reaction apparatus having a batch type reactor as the reactor.

As is shown in FIG. 1, the reaction apparatus comprises the batch type reactor 1 and a distillation column 2. The batch type reactor 1 is pressureproof and has a stirrer 1a and a heater 1b. A raw material supply tube 4 and an extraction tube 5 are connected to the batch type reactor 1. An upper part of the batch type reactor 1 and a column bottom part of the distillation column 2 are connected to each other through an introducing tube 3 such that a gas generating from the batch type reactor 1 can be introduced into the distillation column 2, and that a column bottom liquid in the distillation column 2 can be returned to the batch type reactor 1. An extraction tube 6 to extract distillates is connected to a column top of the distillation column 2.

To begin with, a first reaction is carried out in the absence of either or both of the (poly)alkylene glycol dialkyl ether and the alcohol. The olefin, the (poly)alkylene glycol, and the catalyst, which are raw reaction materials, and further the solvent, if necessary, are charged into the batch type reactor 1 through the raw material supply tube 4. Next, the resultant reaction liquid is heated while stirred to carry out the reaction under conditions of a predetermined temperature and a predetermined pressure, thus synthesizing the (poly)alkylene glycol monoalkyl ether, when either or both of the (poly)alkylene glycol dialkyl ether and the alcohol form as by-products. After the reaction has ended, the stirrer is stopped, and the reaction liquid is allowed to stand stationary and to thereby separate into the (poly)alkylene glycol phase containing the catalyst (lower layer) and the olefin phase containing the (poly)alkylene glycol monoalkyl ether (upper layer). Thereafter, the (poly)alkylene glycol phase is extracted from the batch type reactor 1 through the extraction tube 5. The olefin phase remaining in the batch type reactor 1 is separated into each component by batch distillation. While respective pressures in the batch type reactor 1 and the distillation column 2, the temperature of the olefin phase remaining in the batch type reactor 1, and the reflux ratio of the distillation column 2 are controlled, each component present in the olefin phase is taken out in ascendant order of the boiling point thereof as the distillate from the column top of the distillation column 2 through the extraction tube 6. The unreacted olefin and the alcohol as a by-product are first recovered, and the (poly)alkylene glycol monoalkyl ether is then recovered as a product. The (poly) alkyiene glycol dialkyl ether, which is a by-product, may be either recovered by further distillation or allowed to remain as a distillation bottom in the batch type reactor 1 and to be supplied to the next batch type reaction. In addition, the distillation of the olefin phase may be carried out using distillers (not drawn in the figure) other than the distillation column 2.

Next, an explanation is made on second and subsequent reactions. In the second and subsequent reactions, either or both of the (poly)alkylene glycol dialkyl ether and the alcohol as formed as by-products are supplied to the system of the reaction to carry out the reactions. In addition, the unreacted olefin or the (poly)alkylene glycol phase is recycled to carry out the reactions. The unreacted olefin, the (poly)alkylene glycol phase containing the catalyst, and either or both of the (poly)alkylene glycol dialkyl ether and the alcohol as formed as by-products, all of which are recovered from the previous batch type reaction, are used as raw reaction materials, and further, the olefin and the (poly) alkylene glycol as consumed in the previous reaction are replenished to the raw reaction materials, which are then charged into the batch type reactor 1 through the raw material supply tube 4. Where the (poly)alkylene glycol dialkyl ether was left as the distillation bottom in the batch type reactor 1, the (poly)alkylene glycol dialkyl ether does not need to be supplied through the raw material supply tube 4. After the raw materials have been supplied, the reaction is carried out under the same conditions as of the previous reaction, and each component is separated and recovered under the same conditions as of the previous reaction. By repeating such a batch type reaction, either or both of the (poly)alkylene glycol dialkyl ether and the alcohol, which are by-products, are converted into the (poly)alkylene glycol monoalkyl ether, whereby the (poly)alkylene glycol monoalkyl ether can be obtained with high selectivity and high efficiency from the olefin and the (poly)alkylene glycol. In addition, where impurities such as heavy contents accumulate in the (poly)alkylene glycol phase or olefin phase due to repeating the batch type reaction, the heavy contents can be removed by purging a portion of the (poly)alkylene glycol phase or a portion of the bottom resultant from the distillation of the olefin phase.

Figure 2:
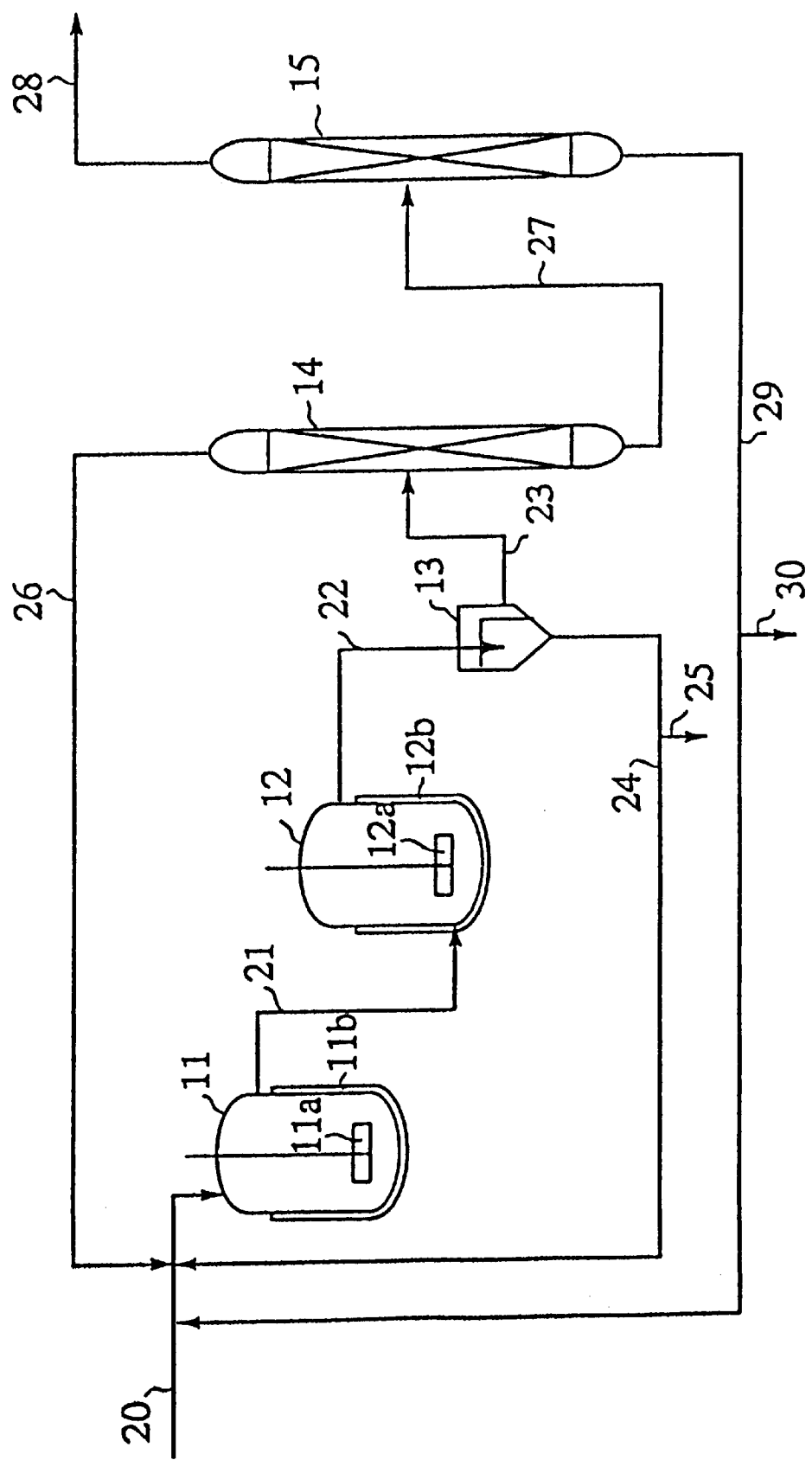
FIG. 2 shows an example of flow charts of reaction apparatuses with continuous vessel type reactors.

Next, referring to FIG. 2, an explanation is made about an embodiment of the production process for the (poly)alkylene glycol monoalkyl ether using a reaction apparatus having a flow type reactor as the reactor.

As is shown in FIG. 2, the reaction apparatus comprises continuous vessel type reactors 11 and 12 and distillation columns 14 and 15. The continuous vessel type reactors 11 and 12 have stirrers 11*a* and 12*a* and heaters 11*b* and 12*b*, respectively. A raw material supply tube 20 is connected to the continuous vessel type reactor 11, and an overflow type introducing tube 21 is connected to an upper part of the continuous vessel type reactor 11. The introducing tube 21 also serves as a raw material supply tube for the continuous vessel type reactor 12. An overflow type introducing tube 22 is connected to an upper part of the continuous vessel type reactor 12 so as to be introduced into a. liquid-liquid separator (settler) 13. The liquid-liquid separator 13 and the distillation column 14 are connected to each other through an introducing tube 23 such that a liquid of the upper layer as separated with the liquid-liquid separator 13 can be introduced into the distillation column 14. In addition, the liquid-liquid separator 13 and the raw material supply tube 20 are connected to each other through an introducing tube 24 such that a liquid of the lower layer as separated with the liquid-liquid separator 13 can be returned to the continuous vessel type reactor 11. An introducing tube 25 is connected to the way of the introducing tube 24. A column bottom part of the distillation column 14 is connected to the distillation column 15 through an introducing tube 27 such that a column bottom liquid in the distillation column 14 can be introduced into the distillation column 15. In addition, a column top of the distillation column 14 and the raw material supply tube 20 are connected to each other through an introducing tube 26 such that distillates from the distillation column 14 can be returned to the continuous vessel type reactor 11. A column bottom part of the distillation column 15 and the raw material supply tube 20 are connected to each other through an introducing tube 29 such that a column bottom liquid in the distillation column 15 can be returned to the continuous vessel type reactor 11. An introducing tube 30 is connected to the way of the introducing tube 29. An introducing tube 28 is connected to a column top of the distillation column 15.

To begin with, the olefin, the (poly)alkylene glycol, and the catalyst, which are raw reaction materials, and further the solvent if necessary, are continuously charged into the continuous vessel type reactor 11 through the raw material supply tube 20. Next, the resultant reaction liquid is heated while stirred to carry out the reaction under conditions of a predetermined temperature and a predetermined pressure, thus synthesizing the (poly)alkylene glycol monoalkyl ether, when either or both of the (poly)alkylene glycol dialkyl ether and the alcohol form as by-products. An overflow portion of the reaction liquid is introduced into the continuous vessel type reactor 12 to further carry out the reaction, and the resultant overflow portion is introduced into the liquid-liquid separator 13. In the liquid-liquid separator 13, the overflow portion is separated into the (poly)alkylene glycol phase containing the catalyst (lower layer) and the olefin phase containing the (poly)alkylene glycol monoalkyl ether, the (poly)alkylene glycol dialkyl ether and the alcohol (upper layer). Thereafter, the (poly)alkylene glycol phase is extracted through the introducing tube 24 and, if need arises, replenished with the (poly)alkylene glycol, as consumed in the reaction, and then charged into the continuous vessel type reactor 11 through the raw material supply tube 20. In addition, if necessary, a portion of the (poly)alkylene glycol phase may be extracted from the introducing tube 25, as connected to the way of the introducing tube 24, to regenerate a portion of the catalyst. In such a case, the catalyst and the (poly)alkylene glycol are recovered from the (poly)alkylene glycol phase as extracted from the introducing tube 25, and the recovered catalyst is regenerated. The regenerated catalyst and the recovered (poly)alkylene glycol are supplied again to the continuous vessel type reactor 11 through the raw material supply tube 20. Where impurities, such as heavy contents and water which form due to side reactions such as dehydration condensation, accumulate in the (poly)alkylene glycol phase, the heavy contents can be removed to outside the system by taking advantage of the extraction of at least a portion of the (poly)alkylene glycol phase for the regeneration of the catalyst, in other words, by purging a portion of the (poly)alkylene glycol phase through the introducing tube 25. The olefin phase of the upper layer in the liquid-liquid separator 13 is introduced into the distillation column 14 through the introducing tube 23. While the pressure in the distillation column 14, the temperature of the olefin phase, and the reflux ratio of the distillation column 14 are controlled, low boiling point components present in the olefin phase, namely, the unreacted olefin and the alcohol which is a by-product, are extracted as distillates from the column top of the distillation column 14 through the introducing tube 26. The olefin and the alcohol, as extracted, are charged into the continuous vessel type reactor 11 through the raw material supply tube 20 after, if need arises, replenished with the olefin as consumed in the reaction. The (poly)alkylene glycol monoalkyl ether, which is a distillation bottom of the distillation column 14, and the (poly)alkylene glycol dialkyl ether, which is a by-product and a distillation bottom of the distillation column 14, are introduced into the distillation column 15 through the introducing tube 27. While the pressure in the distillation column 15, the temperature of the (poly)alkylene glycol monoalkyl ether phase, and the reflux ratio of the distillation column 15 are controlled, the (poly)alkylene glycol monoalkyl ether which is a low boiling point component is extracted as a distillate from the column top of the distillation column 15 through the introducing tube 28. The (poly)alkylene glycol dialkyl ether, which is the distillation bottom of the distillation column 15, is charged into the continuous vessel type reactor 11 through the introducing tube 29 and further through the raw material supply tube 20. Where impurities such as heavy contents accumulate in the (poly)alkylene glycol dialkyl ether phase, the heavy contents can be removed by purging a portion of the (poly)alkylene glycol dialkyl ether phase through the introducing tube 30. In addition, where by-products, such as skeletal isomers of the olefin. dimers of the olefin, polymers of the olefin, and cyclization condensation products of the (poly)alkylene glycol (e.g. dioxane, methyldioxolane), accumulate in the olefin phase, the by-products can be removed, for example, by fitly setting distillation columns and distilling off the by-products (not drawn in the figure) or by purging a portion of the distillation bottom liquid. In this way, when the (poly)alkylene glycol and the olefin are reacted to produce the (poly)alkylene glycol monoalkyl ether, if the crystalline metallosilicate is used as the catalyst and if at least a portion of the used catalyst is regenerated and then recycled as the catalyst for the reaction between the (poly)alkylene glycol and the olefin, the high activity of the catalyst can be maintained, and the (poly)alkylene glycol monoalkyl ether can be obtained stably and efficiently. Particularly, where the long chain olefin is used as the olefin, if the above-mentioned flow type reaction is repeated, either or both of the (poly)alkylene glycol di-higher-alkyl ether and the higher alcohol, which are by-products, are converted into the (poly)alkylene glycol mono-higher-alkyl ether, whereby the (poly)alkylene glycol mono-higher-alkyl ether can be obtained with high selectivity and high efficiency from the long chain olefin and the (poly)alkylene glycol.

The (poly)alkylene glycol monoalkyl ether as obtained in the present invention is useful as a raw material for surfactants.

(Effects and Advantages of the Invention)

In the first production process of the present invention, because the crystalline metallosilicate is used as the catalyst, the (poly)alkylene glycol monoalkyl ether can be produced at a fast reaction rate with high selectivity and high yield. In addition, because at least a portion of the used catalyst is regenerated and then recycled as the catalyst for the reaction, the stationary activity of the catalyst can be obtained.

In addition, the second production process of the present invention is capable of inhibiting the formation of by-products, such as the (poly)alkylene glycol dialkyl ether and the alcohol, and thereby producing the (poly)alkylene glycol monoalkyl ether with high selectivity and high yield.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples.

EXAMPLE 1

Ethylene glycol monododecyl ether was continuously produced using a reaction apparatus as shown in FIG. 2. Stainless-steel-made continuous vessel type reactors of 1,000 ml in capacity having a stirrer and a band heater were used as the continuous vessel type reactors 11 and 12. Overflow lines as shown by the introducing tubes 21 and 22 were set to the continuous vessel type reactors 11 and 12, and an arrangement was made such that the reaction liquid could run from the continuous vessel type reactor 11 to the continuous vessel type reactor 12 and then to the liquid-liquid separator 13 depending on a supply rate of the raw materials as supplied through the raw material supply tube 20. A 15-stage Oldershaw type distillation column with an inner diameter of 32 mm ϕ was used as the distillation column 14, and the introducing tube 23 was connected to the fifth stage from the column top. A reflux device (not drawn in the figure) was set on the column top of the distillation column 14. In addition, a preheater (not drawn in the figure) was set near a connecting part between the introducing tube 23 and the distillation column 14 to heat the reaction liquid as supplied from the introducing tube 23 to the distillation column 14. A packed column, which was made of stainless steel and had an inner diameter of 20 mm ϕ and a height of 500 mm, was used as the distillation column 15, and stainless-steel-made Dixon packing of 1.5 mm ϕ was used as the packing. In addition, a reflux device (not drawn in the figure) was set on the column top of the distillation column 15. The introducing tube 27 was connected to a central portion of the distillation column 15, and a preheater (not drawn in the figure) was set near a connecting part to heat the reaction liquid as supplied from the introducing tube 27 to the distillation column 15. In addition, vacuum devices were set to the distillation columns 14 and 15 respectively to carry out the distillation under vacuum.

A mixture of 268 g of 1-dodecene, 298 g of monoethylene glycol, and 32.7 g of BEA type zeolite (trade name: VALFOR CP 811BL-25, atomic ratio of Si to Al: 12.5, specific surface area: 750 $m^2$/g, hereinafter abbreviated as catalyst), made of PQ Co., Ltd., as the catalyst was charged into each of the continuous vessel type reactors 11 and 12, and the stirrers were run at a revolution number of 600 rpm. The temperature inside the reactors was elevated to 150° C., and thereafter, this temperature was maintained. The raw materials and the catalyst were supplied from the raw material supply tube 20 to the continuous vessel type reactor 11 at supply rates of 268 g/hr for 1-dodecene, 298 g/hr for monoethylene glycol, and 32.7 g/hr for the catalyst to initiate the reaction, wherein the catalyst was suspended into monoethylene glycol before supplied. The reaction liquid was transferred to the liquid-liquid separator 13 through the introducing tube 22 and separated into a monoethylene glycol phase containing the catalyst and an olefin phase containing monoethylene glycol monododecyl ether. The monoethylene glycol phase was recycled to the continuous vessel type reactor 11 through the introducing tube 24, when 5 wt % of a flow rate was purged from the introducing tube 25 to outside the system. On the other hand, the olefin phase was supplied to the distillation column 14 through the introducing tube 23. Operational conditions of the distillation column 14 were as follows: column top pressure=10 mmHg, column bottom temperature=185° C., column top temperature=87° C., reflux ratio=3. The main distillate from the distillation column 14 was unreacted and isomerized dodecene, and was recycled to the reactor 11 through the introducing tube 26. The distillation residue of the distillation column 14 was supplied to the distillation column 15 through the introducing tube 27. Operational conditions of the distillation column 15 were as follows: column top pressure=2 mmHg, column bottom temperature=228° C., column top temperature=126° C., reflux ratio=0.5. The main distillate from the distillation column 15 was objective monoethylene glycol monododecyl ether, which was recovered as a product through the introducing tube 28. The main distillation residue of the distillation column 15 was monoethylene glycol didodecyl ether, which was recycled to the continuous vessel type reactor 11 through the introducing tube 29. In this example, no purge of a portion of the distillation residue of the distillation column 15 through the introducing tube 30 was carried out. After the initiation of the reaction, the respective amounts of the new raw materials (1-dodecene and monoethylene glycol) and the new catalyst, as supplied from the raw material supply tube 20, were controlled depending on the respective flow rates of the recovered raw materials and catalyst, as recycled through the introducing tubes 24, 26, and 29, such that the composition of the raw materials as supplied to the continuous vessel type reactor 11 could be 3/1 as the molar ratio of monoethylene glycol/dodecene, 10 wt % as the amount of the catalyst in the monoethylene glycol phase, and 1 $hr^{-1}$ as the liquid hourly space velocity (LHSV) as the flow rate of the supplied liquid in the reactor 11.

The monoethylene glycol phase, which contained the catalyst and had been continuously purged from the introducing tube 25 to outside the system, was collected into vessels every twelve hours. This purged liquid containing the catalyst was poured onto a flat type evaporating dish to evaporate most of monoethylene glycol with a vacuum dryer, whereby the catalyst was dried until solidified, and the catalyst was then regenerated by calcining it for 3 hours at 600° C. under an air atmosphere in a muffle furnace. When the regenerated catalyst was obtained for the first time after the initiation of the reaction (about 24 hours after the initiation of the reaction), a new lot of the catalyst as supplied from the raw material supply tube 20 was switched to the regenerated catalyst, and since then, the operation of the continuous reaction apparatus was continued using the regenerated catalyst.

Two hundred hours after the initiation of the operation of the continuous reaction apparatus under the above-mentioned operational conditions, the respective amounts of 1-dodecene, monoethylene glycol, and the regenerated catalyst, as newly supplied to the raw material supply tube 20, were 24.8 g/hr, 23.3 g/hr, and 1.63 g/hr. In addition, the amount of the product as recovered through the introducing tube 28 was 33.4 g/hr. As a result of the analysis of this product by gas chromatography, the product contained dodecanol in a proportion of 0.30 wt % and diethylene glycol monododecyl ether in a proportion of 1.2 wt %. At this time, the flow rate of the recycled liquid running through the introducing tube 29 was 23.1 g/hr. The flow rate of the recycled liquid running through the introducing tube 26 was 223.5 g/hr, and this recycled liquid contained dodecanol in a proportion of 0.13 wt %. The total yield of ethylene glycol monododecyl ether and diethylene glycol monododecyl ether, relative to 1-dodecene as supplied, was 98 mol %.

Five hundred hours after the subsequent continuation of the operation, the amount of the product as recovered through the introducing tube 28 was 33.2 g/hr, and as a result of the analysis of this product by gas chromatography, the product contained dodecanol in a proportion of 0.31 wt % and diethylene glycol monododecyl ether in a proportion of 1.4 wt %. At this time, the total yield of ethylene glycol monododecyl ether and diethylene glycol monododecyl ether, relative to 1-dodecene as supplied, was 98 mol %.

Comparative Example 1

The continuous reaction apparatus was operated to produce monoethylene glycol monododecyl ether in the same way as of Example 1 except that no purge from the introducing tube 25 was carried out, and that no addition of the new or regenerated catalyst from the raw material supply tube 20 was carried out. One hundred hours after the initiation of the reaction, the amount of the product as recovered through the introducing tube 28 was 30.0 g/hr, and 200 hours after the initiation of the reaction, the amount of the product as recovered through the introducing tube 28 reduced to 11.4 g/hr. Thereafter, because the amount of the formation of monoethylene glycol monododecyl ether greatly reduced, the continuous reaction apparatus could not stably be operated.

<Recovery of the (Poly)alkylene Glycol>

Referential Example 1

A mixture of 10.0 g of BEA type zeolite (trade name: VALFOR CP 811BL-25, atomic ratio of Si to Al: 12.5, specific surface area: 750 m$^2$/g, hereinafter abbreviated as catalyst), made of PQ Co., Ltd., as the catalyst and 90.0 g of monoethylene glycol was charged into a 200-ml eggplant-shaped flask, which was then set to a rotary evaporator as equipped with a vacuum device and an oil bath for heating. The oil bath was set at 180° C., and the eggplant-shaped flask was then immersed into the oil bath, and the evaporator was then rotated. Thereafter, the vacuum device was run and controlled to a pressure under which a distillate could be obtained. The operation was ended when about 50 g of distillate was collected. A slurry, which remained in the eggplant-shaped flask and contained the catalyst, was filtered off with a membrane filter, thus obtaining a bottom liquid. Each of the bottom liquid and the distillate was analyzed by gas chromatography to determine the contents of by-products other than monoethylene glycol. Results are shown in Table 1.

Referential Examples 2 and 3

The recovery of monoethylene glycol was carried out in the same way as of Referential Example 1 except that the temperature of the oil bath was 150° C. or 120° C. Results are shown in Table 1.

Referential Example 4

The recovery of monoethylene glycol was carried out in the same way as of Referential Example 1 except that the temperature of the oil bath was 200° C., and that the pressure was normal pressure. Results are shown in Table 1.

TABLE 1

| Referential Example | Recovery temperature (° C.) | Pressure (mmHg) | By-product content (wt %) | | | | |
|---|---|---|---|---|---|---|---|
| | | | Distillate | | | Bottom liquid | |
| | | | Methyl-dioxolane | Dioxane | Diethylene glycol | Diethylene glycol | Triethylene glycol |
| 1 | 180 | 400 | 0.7 | 0.3 | 0.2 | 1.0 | 0.1 |
| 2 | 150 | 150 | 0.1 | 0.0 | 0.0 | 0.2 | 0.0 |
| 3 | 120 | 40 | 0.0 | 0.0 | 0.0 | 0.1 | 0.0 |
| 4 | 200 | 760 | 5.9 | 7.3 | 0.8 | 8.4 | 0.7 |

Referential Example 5

The separation and recovery of the catalyst and monoethylene glycol from the mixed slurry of the catalyst and monoethylene glycol was carried out using an instantaneous vacuum dryer (trade name: CRUX System, made by Hosokawa Mikron Co., Ltd.) as the dryer. The instantaneous vacuum dryer comprises: a heating tube consisting of a stainless steel pipe (inner diameter: 8 mm, length: 8 m); a collector; a bag filter; and a condenser. The heating tube is covered with a jacket such that an outer wall of the heating tube can be heated by supplying steam or a heating medium into the jacket. An end of the heating tube is connected to the collector, and the bag filter is set on an upper part of the collector and further connected to the condenser. Respective temperatures of the heating tube, the collector, the bag filter, and the condenser can be managed independently of each other. The condenser is further connected to a vacuum pump such that respective pressures of the condenser and the collector can be controlled. The mechanism is as follows: the slurry, in which solid particles are dispersed in the liquid, is supplied from an end of the heating tube using a metering pump, thus thermally evaporating the liquid with the heating tube as well as drying the solid particles with the heating tube, and the evaporated gas is led to the condenser through the bag filter and then liquefied, thus recovering the liquid, and the dried solid particles are collected with the collector. Operational conditions of the instantaneous vacuum dryer were set as follows: the outer wall temperature of the heating tube was 225° C., the temperatures of the collector and the bag filter were both 130° C., the temperature of the condenser was 1° C., and the pressures of the collector and the condenser were both 10 mmHg. A slurry was obtained by mixing 2.0 kg of the catalyst (BEA type zeolite made by PQ Co., Ltd.), as used in Referential Example 1, and 18.0 kg of monoethylene glycol. This slurry was supplied to the heating tube at a rate of 12.5 kg/hr using the metering pump. Slightly later than the initiation of the supply, a powder began to be collected into the collector, and a condensate began to distill into the condenser. After the entirety of the slurry had been supplied, the operation of the instantaneous vacuum dryer was stopped, and the recovered powder and condensate were taken out, and the weights thereof were measured. As a result, the recovered powder weighed 17.4 kg, and the recovered condensate weighed 2.5 kg. The recovered powder was subjected to thermogravimetric analysis to measure the catalyst content (nonvolatile content). As a result, the catalyst content was 80.0 wt %. The recovered condensate was analyzed by gas chromatography to determine the contents of by-products other than monoethylene glycol. As a result, the contents of the by-products in the condensate were 0.09 wt % for methyldioxolane, 0.16 wt % for dioxane, and 0.10 wt % for diethylene glycol.

<Regeneration of the Catalyst>

Referential Example 6

The monoethylene glycol phase, which contained the catalyst and had been continuously purged from the introducing tube 25 to outside the system in Example 1, was collected. This purged liquid containing the catalyst was poured onto a flat type evaporating dish to evaporate most of monoethylene glycol under conditions of 150° C. and 200 mmHg with a vacuum dryer, whereby the catalyst was dried until solidified, and the catalyst was then calcined for 3 hours at 500° C. under an air atmosphere in a muffle furnace. The calcined catalyst was pale yellow, and as a result of organic elemental analysis thereof, the carbon content in the calcined catalyst was only 0.1 wt %.

Referential Example 7

The regeneration of the catalyst was carried out in the same way as of Referential Example 6 except that the calcination temperature was 600° C. The calcined catalyst was white, and as a result of organic elemental analysis thereof, no carbon was detected.

Referential Example 8

The regeneration of the catalyst was carried out in the same way as of Referential Example 6 except that the calcination temperature was 400° C. The calcined catalyst was black, and as a result of organic elemental analysis thereof, the carbon content in the calcined catalyst was 1.2 wt %.

EXAMPLE 2

Ethylene glycol monododecyl ether was continuously produced using a reaction apparatus as shown in FIG. 2. Stainless-steel-made continuous vessel type reactors of 1,000 ml in capacity having a stirrer and a band heater were used as the continuous vessel type reactors 11 and 12. Overflow lines as shown by the introducing tubes 21 and 22 were set to the continuous vessel type reactors 11 and 12, and an arrangement was made such that the reaction liquid could run from the continuous vessel type reactor 11 to the continuous vessel type reactor 12 and then to the liquid-liquid separator 13 depending on a supply rate of the raw materials as supplied through the raw material supply tube 20. A 15-stage Oldershaw type distillation column with an inner diameter of 32 mm φ was used as the distillation column 14, and the introducing tube 23 was connected to the fifth stage from the column top. A reflux device (not drawn in the figure) was set on the column top of the distillation column 14. In addition, a preheater (not drawn in the figure) was set near a connecting part between the introducing tube 23 and the distillation column 14 to heat the reaction liquid as supplied from the introducing tube 23 to the distillation column 14. A packed column, which was made of stainless steel and had an inner diameter of 20 mm φ and a height of 500 mm, was used as the distillation column 15, and stainless-steel-made Dixon packing of 1.5 mm φ was used as the packing. In addition, a reflux device (not drawn in the figure) was set on the column top of the distillation column 15. The introducing tube 27 was connected to a central portion of the distillation column 15, and a preheater (not drawn in the figure) was set near a connecting part to heat the reaction liquid as supplied from the introducing tube 27 to the distillation column 15. In addition, vacuum devices were set to the distillation columns 14 and 15 respectively to carry out the distillation under vacuum.

A mixture of 268 g of 1-dodecene, 298 g of monoethylene glycol, and 32.7 g of BEA type zeolite (trade name: VALFOR CP 811BL-25, atomic ratio of Si to Al: 12.5, specific surface area: 750 m²/g, hereinafter abbreviated as catalyst), made of PQ Co., Ltd., as the catalyst was charged into each of the continuous vessel type reactors 11 and 12, and the stirrers were run at a revolution number of 600 rpm. The temperature inside the reactors was elevated to 150° C., and thereafter, this temperature was maintained. The raw materials and the catalyst were supplied from the raw material supply tube 20 to the continuous vessel type reactor 11 at supply rates of 268 g/hr for 1-dodecene, 298 g/hr for monoethylene glycol, and 32.7 g/hr for the catalyst to initiate the reaction, wherein the catalyst was suspended into monoethylene glycol before supplied. The reaction liquid was transferred to the liquid-liquid separator 13 through the introducing tube 22 and separated into a monoethylene glycol phase containing the catalyst and an olefin phase containing monoethylene glycol monododecyl ether. The monoethylene glycol phase was recycled to the continuous vessel type reactor 11 through the introducing tube 24, when 5 wt % of a flow rate was purged from the introducing tube 25 to outside the system. On the other hand, the olefin phase was supplied to the distillation column 14 through the introducing tube 23. Operational conditions of the distillation column 14 were as follows: column top pressure=10 mmHg, column bottom temperature=185° C., column top temperature=87° C., reflux ratio=3. The main distillate from the distillation column 14 was unreacted and isomerized dodecene, and was recycled to the reactor 11 through the introducing tube 26. The distillation residue of the distillation column 14 was supplied to the distillation column 15 through the introducing tube 27. Operational conditions of the distillation column 15 were as follows: column top pressure=2 mmHg, column bottom temperature=228° C., column top temperature=126° C., reflux ratio=0.5. The main distillate from the distillation column. 15 was objective monoethylene glycol monododecyl ether, which was recovered as a product through the introducing tube 28. The main distillation residue of the distillation column 15 was monoethylene glycol didodecyl ether, which was recycled to the continuous vessel type reactor 11 through the introducing tube 29. In this example, no purge of a portion of the distillation residue of the distillation column 15 through the introducing tube 30 was carried out. After the initiation of the reaction, the respective amounts of the new raw materials (1-dodecene and monoethylene glycol) and the new catalyst, as supplied from the raw material supply tube 20, were controlled depending on the respective flow rates of the recovered raw materials and catalyst, as recycled through the introducing tubes 24, 26, and 29, such that the composition of the raw materials as supplied to the continuous vessel type reactor 11 could be 3/1 as the molar ratio of monoethylene glycol/dodecene, 10 wt % as the amount of the catalyst in the monoethylene glycol phase, and 1 hr$^{-1}$ as the liquid hourly space velocity (LHSV) as the flow rate of the supplied liquid in the reactor 11.

Two hundred hours after the initiation of the operation of the continuous reaction apparatus under the above-mentioned operational conditions, the respective amounts of 1-dodecene, monoethylene glycol, and the catalyst, as newly supplied to the raw material supply tube 20, were 24.8 g/hr, 23.3 g/hr, and 1.63 g/hr. In addition, the amount of the product as recovered through the introducing tube 28 was 33.4 g/hr. As a result of the analysis of this product by gas chromatography, the product contained dodecanol in a proportion of 0.30 wt % and diethylene glycol monododecyl ether in a proportion of 1.2 wt %. At this time, the flow rate of the recycled liquid running through the introducing tube 29 was 23.1 g/hr. The flow rate of the recycled liquid running through the introducing tube 26 was 223.5 g/hr, and this recycled liquid contained dodecanol in a proportion of 0.13 wt %. The total yield of ethylene glycol monododecyl ether and diethylene glycol monododecyl ether, relative to 1-dodecene as supplied, was 98 mol %.

Five hundred hours after the subsequent continuation of the operation, the amount of the product as recovered through the introducing tube 28 was 33.2 g/hr, and as a result of the analysis of this product by gas chromatography, the product contained dodecanol in a proportion of 0.31 wt % and diethylene glycol monododecyl ether in a proportion of 1.4 wt %. At this time, the total yield of ethylene glycol monododecyl ether and diethylene glycol monododecyl ether, relative to 1-dodecene as supplied, was 98 mol %.

EXAMPLE 3

Ethylene glycol monotetradecyl ether was continuously produced using the same reaction apparatus as of Example 2. A mixture of 291 g of 1-tetradecene, 276 g of monoethylene glycol, and 30.7 g of BEA type zeolite (trade name: VALFOR CP 811BL-25, atomic ratio of Si to Al: 12.5, specific surface area: 750 m$^2$/g, hereinafter abbreviated as catalyst), made of PQ Co., Ltd., as the catalyst was charged into each of the reactors 11 and 12, and the stirrers were run at a revolution number of 600 rpm. The temperature. inside the reactors was elevated to 150° C., and thereafter, this temperature was maintained. The raw materials and the catalyst were supplied from the raw material supply tube 20 to the continuous vessel type reactor 11 at supply rates of 291 g/hr for 1-tetradecene, 276 g/hr for monoethylene glycol, and 30.7 g/hr for the catalyst to initiate the reaction. The subsequent reaction operation was carried out in the same way as of Example 2, wherein operational conditions of the distillation column 14 were as follows: column top pressure=10 mmHg, column bottom temperature=210° C., column top temperature=120° C., reflux ratio=3, and operational conditions of the distillation column 15 were as follows: column top pressure=1 mmHg, column bottom temperature=240° C., column top temperature=145° C., reflux ratio=0.5.

After the initiation of the reaction, in the same way as of Example 2, the respective amounts of the new raw materials and catalyst as supplied from the raw material supply tube 20 were controlled depending on the respective flow rates of the recovered raw materials and catalyst, as recycled through the introducing tubes 24, 26, and 29, such that the composition of the raw materials as supplied to the continuous vessel type reactor 11 could be 3/1 as the molar ratio of monoethylene glycol/tetradecene, 10 wt % as the amount of the catalyst in the monoethylene glycol phase, and 1 hr$^{-1}$ as the liquid hourly space velocity (LHSV) as the flow rate of the supplied liquid in the reactor 11.

Two hundred hours after the initiation of the operation of the continuous reaction apparatus under the above-mentioned operational conditions, the respective amounts of 1-tetradecene, monoethylene glycol, and the catalyst, as newly supplied to the raw material supply tube 20, were 23.3 g/hr, 20.6 g/hr, and 1.53 g/hr. In addition, the amount of the product as recovered through the introducing tube 28 was 30.0 g/hr. As a result of the analysis of this product by gas chromatography, the product contained tetradecanol in a proportion of 0.33 wt % and diethylene glycol monotetradecyl ether in a proportion of 1.4 wt %. At this time, the flow rate of the recycled liquid running through the introducing tube 29 was 20.2 g/hr. The flow rate of the recycled liquid running through the introducing tube 26 was 250.7 g/hr, and this recycled liquid contained tetradecanol in a proportion of 0.12 wt %. The total yield of ethylene glycol monotetradecyl ether and diethylene glycol monotetradecyl ether, relative to 1-tetradecene as supplied, was 97 mol %.

Five hundred hours after the subsequent continuation of the operation, the amount of the product as recovered through the introducing tube 28 was 29.9 g/hr, and as a result of the analysis of this product by gas chromatography, the product contained tetradecanol in a proportion of 0.36 wt % and diethylene glycol monotetradecyl ether in a proportion of 1.6 wt %. At this time, the total yield of ethylene glycol monotetradecyl ether and diethylene glycol monotetradecyl ether, relative to 1-tetradecene as supplied, was 97 mol %.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing a (poly)alkylene glycol monoalkyl ether, comprising the steps of:
   a) reacting an olefin and a (poly)alkylene glycol in the presence of a catalyst comprising a crystalline metallosilicate to obtain a (poly)alkylene glycol phase and an olefin phase, wherein the step of reacting the olefin and (poly)alkylene glycol comprises the step of selecting an olefin that dissolves into the (poly)alkylene glycol with mere slight solubility such that the step of reacting is carried out in a heterogeneous state, and wherein the step of selecting the olefin comprises the step of selecting a long chain olefin or an olefin of 8 to 30 in number of carbon atoms with an ethylenically unsaturated bond; then
   b) separating the (poly)alkylene glycol phase and the olefin phase from each other, wherein the olefin phase includes (poly)alkylene glycol monoalkyl ether, which is the product, wherein the olefin phase further includes a (poly)alkylene glycol dialkyl ether and an alcohol, both of which are by-products;
   c) separating the (poly)alkylene glycol monoalkyl ether and one or both of the polyalkylene glycol dialkyl ether and the alcohol from the olefin phase;
   d) recovering the (poly)alkylene glycol monoalkyl ether as the product; and
   e) recovering one or both of the (poly)alkylene glycol dialkyl ether and the alcohol and then recycling said recovered one or both of the (poly)alkylene glycol dialkyl ether and the alcohol back to said step of reacting.

2. A process according to claim 1, wherein: said (poly)alkylene glycol monoalkyl ether is a (poly)alkylene glycol mono-higher-alkyl ether; said (poly)alkylene glycol dialkyl ether is a (poly)alkylene glycol di-higher-alkyl ether; and said alcohol is a higher alcohol.

\* \* \* \* \*